United States Patent [19]
Fraissl

[11] 4,283,115
[45] Aug. 11, 1981

[54] BEAM SPLITTERS FOR ENDOSCOPES COMPRISING A DUAL OBSERVATION SYSTEM

[75] Inventor: Klaus Fraissl, Forst, Fed. Rep. of Germany

[73] Assignee: Richard Wolf GmbH, Knittlengen, Fed. Rep. of Germany

[21] Appl. No.: 54,668

[22] Filed: Jul. 5, 1979

[30] Foreign Application Priority Data

Jun. 28, 1978 [DE] Fed. Rep. of Germany ....... 7822629

[51] Int. Cl.³ ............................................. G02B 27/14
[52] U.S. Cl. ......................................... 350/171; 128/4
[58] Field of Search ................. 350/171, 173, 169, 33, 350/34, 54, 52, 19, 354–357, 362, 314, 315, 316, 318; 128/4

[56] References Cited

U.S. PATENT DOCUMENTS

| | | | |
|---|---|---|---|
| 2,565,514 | 8/1951 | Pajes | 350/356 |
| 3,307,897 | 3/1967 | Lohmann | 350/356 |
| 3,552,824 | 1/1971 | Kiss | 350/354 |
| 3,994,557 | 11/1976 | Hopkins | 350/33 |

FOREIGN PATENT DOCUMENTS

1276205 8/1968 Fed. Rep. of Germany ........... 350/355
1284711 9/1972 United Kingdom .................... 350/354

OTHER PUBLICATIONS

Zielinski, Benjamin, et al., "New Inventions", *The Lancet*, Apr., 1963, pp. 924–925.
Metavac Inc., Advertisement, "Gradient Neutral Density Filters", Jul., 1974.

*Primary Examiner*—Jon W. Henry
*Attorney, Agent, or Firm*—Kinzer, Plyer, Dorn & McEachran

[57] ABSTRACT

This invention relates to beam splitters for use with endoscopes of the kind comprising a dual observation system whereby the image may optionally be adjusted for different proportions of the light intensity for the observer and the joint observer or a film or television camera by means of the optical system of the endoscope.

According to the invention the beam splitter comprises two thin glass plates having a partial specular finish or partial reflection, at least one of said plates being shiftable to bring the partial specular finish in confrontation to an angled position in the beam path of the endoscope.

5 Claims, 8 Drawing Figures

BEAM SPLITTERS FOR ENDOSCOPES COMPRISING A DUAL OBSERVATION SYSTEM

BACKGROUND OF THE INVENTION

The present invention relates to beam splitters for use with endoscopes of the kind comprising a dual observation system whereby the image may optionally be adjusted for different proportions of the light intensity for the observer and the joint observer or a film or television camera by means of the optical system of the endoscope.

It is known in the case of endoscopes comprising a dual observations system, for example of an articulated optical system, to switch a partially transparent prism into the beam path of the endoscope, whereby the light strength of the image is divided, for example, into 50% for the doctor working with the endoscope and 50% for the co-observer. Since film or television cameras which require a high light intensity are also frequently to be connected to the co-observation system, it has already been proposed to replace the conventional beam splitter prism by a second prism having a higher partial reflectivity for the co-observation system, or to combine the two prisms and to place these at will in the beam path of the endoscope by displacing them in accordance with the required beam division.

It is an object of the invention also to obtain a different beam division for endoscopes of the kind specified in the foregoing by optional insertion of beam splitters into the beam path of the endoscope and concomitantly in applying particularly uncomplicated devices.

SUMMARY OF THE INVENTION

Accordingly, in an endoscope of the kind comprising a dual observation system whereby the image may optionally be adjusted for different proportionsof the light intensity for the observer and the joint observer or a film or television camera by means of the optical system of the endoscope, the invention consists in a beam splitter comprising two thin glass plates having a partial specular finish or partial reflection, at least one of said plates being shiftable to bring the partial specular finish in confrontation to an angled position in the beam path of the endoscope.

The beam splitter operating with different division of the image intensity thus consists of two uncomplicated small thin glass plates comprising an identical or dissimilar partial specular finish or partial reflection, which may be produced in uncomplicated manner and whereof the one small plate, or both small plates in adjacent position and with the partial reflective coatings in juxtaposition, may be switched into the beam path of the endoscope, that is by means of a tipping displacement of the one small glass plate towards the other or by displacement of the one small glass plate on the other which is constantly situated in the beam path.

Instead of two small glass plates, there may be an advantage possibly to make use of a single small glass plate only, which over a partial surface is equipped with an attenuated partial reflective coating and over the other partial surface with a denser partial reflective coating, so that by displacement within its own plane, the small glass plate may be switched with the one areal portion or the other into the beam path of the endoscope, so that a particular beam division, for example 50:50% in one case, and in another case a differing division, for example 25:75%, is available for film takes or television recordings.

The procedure applied in accordance with another possibility is that a small glass plate provided with a partial reflective coating is joined along an areal portion to a second small glass plate mirror-coated along a smaller surface portion, and that the areal portion without the second small glass plate, and thus also the areal portion with the small glass plate joined thereto, may optionally be placed in the beam path of the endoscope, a displacement within the plane of the small glass plates or a pivotal displacement around the central section, being possible in this case as well as in the case cited in the foregoing.

BRIEF DESCRIPTION OF THE DRAWINGS

The invention is described in the following with reference to the accompanying drawings which diagrammatically illustrate different embodiment thereof and in which.

DETAILED DESCRIPTION OF PREFERRED EMBODIMENTS

Figure 1:
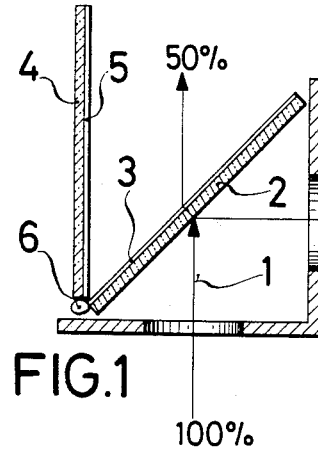
FIG. 1 shows a section through a first embodiment.
Figure 3:
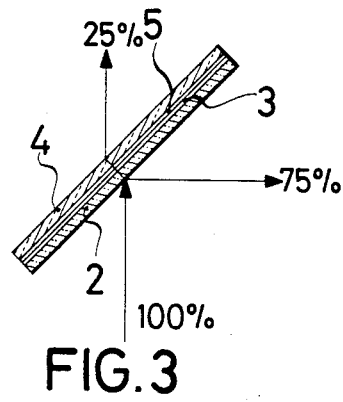
FIG. 3 is an explanatory view,
FIGS. 4, 5 and 7 respectively show sections through three further embodiments.

Referring now to the drawings, according to FIG. 1, a small thin glass plate 2 which at the side facing away from the beam incidence is provided with a partially reflective layer 3 applied by vaporisation, for example consisting of silver, aluminium, chromium or other material. In the example, the coating application 3 is so selected that an image light intensity of 50% is ducted to the doctor actually observing with the endoscope, (not illustrated) to which the splitter is fitted, and that the same image brightness of 50% is reflected towards the co-observer. The small plate 2, 3 may have co-ordinated with it an identical small glass plate 4 comprising a partially reflective layer 5, which may be brought into contact with the small plate 2 with the partially reflective coating 5 facing towards the coating 3 around the axis 6, which is why no more than 25% of the image brightness is radiated to the direct observer and 75% is reflected to the co-observer or to a film or television camera, as shown in FIG. 3.

Figure 2:
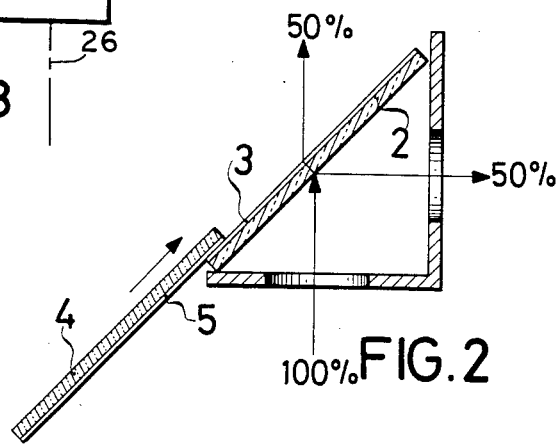
FIG. 2 shows a section through a second embodiment.

Instead of the hinged mounting of the small glass plate 4 according to FIG. 1, the procedure applied according to FIG. 2 may also be such that for increased reflection towards the co-observer or rather towards the film or television camera, the small glass plate 4 is pushed over the small glass plate 2, so that the result of FIG. 3 is again obtained.

It is obviously possible moreover to select the partial specular finish or partial reflectivity in such manner that other ratios are obtained for the transmitted and reflected intensities of image brightness.

Figure 4:
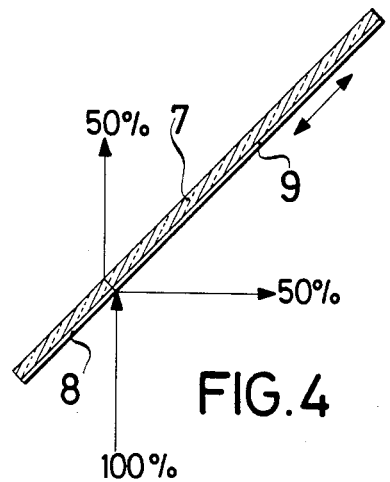

According to FIG. 4, the two small glass plates 2 and 4 of FIGS. 1 and 2, are combined into one small glass plate 7 in one plane, and an areal portion is equipped with a partially reflective coating 8 whereby the image brightness is divided evenly for example, whereas the other areal portion is equipped with a more intensively reflective coating 9 which, after insertion into the beam path of the endoscope, reflects for example 90% of the image brightness towards the co-observer or rather towards a film or television camera, and allows no more than 10% to pass through towards the observing doctor.

Figure 5:
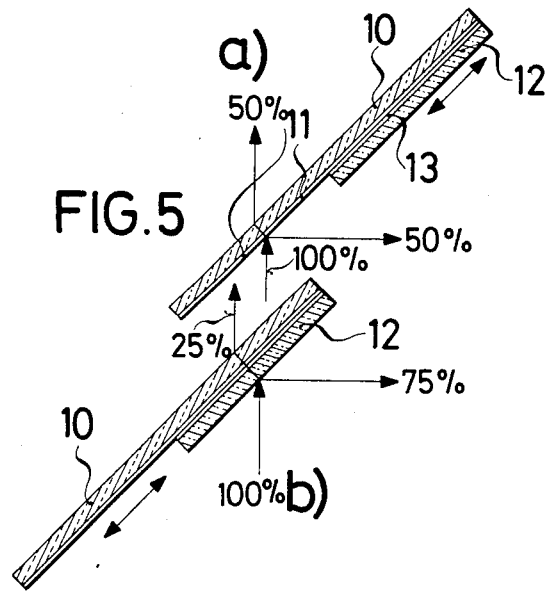

Furthermore, it is also possible to proceed in accordance with FIG. 5, in such manner that a small glass plate 10% is equipped with a constantly partially reflecting coating 11 throughout its surface and that an areal portion has joined to it a second small glass plate 12 having an identical or dissimilar partially reflecting coating 13, the coatings 11 and 12 being in mutual contact. In the position a of FIG. 5, the image brightness is split fifty-fifty for example. After displacing the combined small plates 10 and 11 in their plane into the position b, what occurs is a different image brightness division, for example in the ratio of 25:75%.

It will be understood that the small glass plates according to the embodiments may be produced in particularly uncomplicated manner and may moreover by simple means (not illustrated) be placed in positions of differing ratio of division of the image brightness.

It is also possible to secure a continuous varying ratio between the transmitted and reflected proportions of light. To this end, and in accordance with the embodiment of FIG. 6, a small thin glass plate is equipped with a partially reflective layer 15, e.g. by a cathodic vaporisation process, whereof the thickness and thus the partial reflective capacity rises from the one side to the oppositely situated side of the small glass plate. This small plate set an angle of inclination to the beam path of the endoscope, may be displaced in the plane of the angle of inclination, so that a continuously varying divisional ratio is obtained thereby, i.e. an infinitely variable adjustment of the beam splitter ratio is possible.

Figure 6:
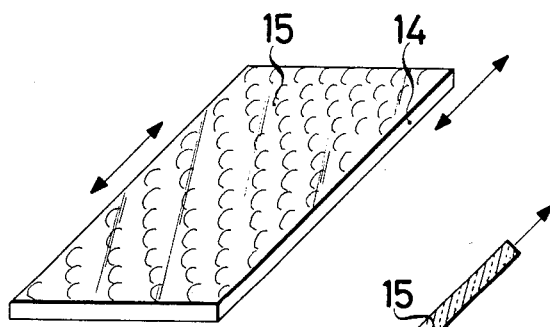
FIG. 6 is a perspective view of one of the plates shown in FIG. 7.
Figure 7:
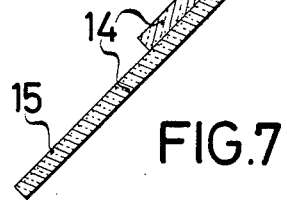

According to FIG. 7, it is also possible to displace two small plates of glass 14 a shown in FIG. 6 with respect to each other with the partial reflecting layers 15 in mutual contact, to secure an improved image mixing action under infinitely variable adjustment of the beam splitter ratio.

The reflection of a partially reflecting coating of a small glass plate or of two adjacent small glass plates may also remain in a constantly identical position with respect to the beam path of the endoscope. The desirable variation of the partial reflection ratio is then varied as a function of an appropriate coating material, by applying an electrical voltage to the coating, whereof the value determines the ratio between the transmitted and reflected light portions. An arrangement to doing this may be set up by any person skilled in the art and thus may take various well-known forms for this reason these arrangements, well-known per se, have not been illustrated.

The variation of the ratio may also occur for particular coating materials by the fact that the coating is irradiated with varying light intensity of the image illumination, thereby altering the partial reflection.

Figure 8:
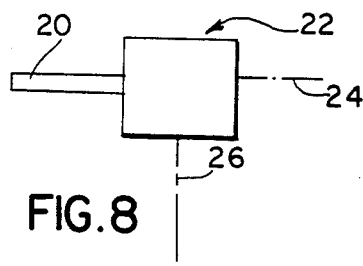
FIG. 8 is a diagrammatic view of a typical endoscope in which the present invention may be used.

A typical endoscope unit having dual observation capability is shown in FIG. 8 for illustrative purposes only, in which the beam splitter of the present invention may be used. The endoscope per se is identified by reference character 20 supported by a housing assembly 22 in which the beam splitter may be located. One observer will be at 24 at one end of the instrument assembly while the other observer will be at 26.

I claim:

1. In an endoscope of the kind comprising a dual observation system whereby the image may optionally be adjusted for different proportions of the light intensity for the observer and the joint observer or a film or television camera by means of the optical system of the endoscope, a beam splitter comprising two thin glass plates each having a partial reflective coating, at least one of said plates being shiftable to bring its partial reflective coating in confrontation to an angled position in the beam path of the endoscope.

2. A beam splitter according to claim 1, wherein said two small glass plates are locatable in mutual congruence with their partial mirror coatings facing towards each other, by displacing one of said glass plates with respect to the other said glass plate.

3. A beam splitter according to claim 1, wherein said two small glass plates are combined in one plane into a combined glass plate which over a partial surface is provided with a less dense partial reflecting coating and over the other partial surface is provided with a denser partial reflecting coating.

4. A beam splitter according to claim 1, wherein one of said small glass plates is provided with a partial reflecting coating and is congruent to an areal portion only of the second one of said small glass plates.

5. A beam splitter according to claim 1, wherein one of said small thin glass plates is coated with a partial reflective coating progressively denser in substantially continuous manner from one side towards the oppositely situated side.

* * * * *